(12) United States Patent
Hitch et al.

(10) Patent No.: US 7,267,801 B2
(45) Date of Patent: Sep. 11, 2007

(54) PIPETTE TIP BOX SHUCKING METHOD AND APPARATUS

(75) Inventors: Jonn Hitch, Indianapolis, IN (US); Rick A. Spencer, Indianapolis, IN (US)

(73) Assignee: Beckman Coulter, Inc., Fullerton, CA (US)

( * ) Notice: Subject to any disclaimer, the term of this patent is extended or adjusted under 35 U.S.C. 154(b) by 727 days.

(21) Appl. No.: 10/238,301

(22) Filed: Sep. 10, 2002

(65) Prior Publication Data
US 2003/0017604 A1  Jan. 23, 2003

Related U.S. Application Data

(63) Continuation of application No. 09/324,936, filed on Jun. 3, 1999, now abandoned.

(51) Int. Cl.
*B01L 3/02* (2006.01)
(52) U.S. Cl. .......................... 422/100; 422/63; 422/64; 422/65; 422/99; 422/101; 436/43; 436/47; 73/864.11; 73/864.14
(58) Field of Classification Search ................. 436/36, 436/180; 422/99–101, 63–65; 73/864.11, 73/864.14
See application file for complete search history.

(56) References Cited

U.S. PATENT DOCUMENTS

| | | | |
|---|---|---|---|
| 5,104,621 A | 4/1992 | Pfost et al. | |
| 5,226,462 A | 7/1993 | Carl | |
| 5,497,670 A | 3/1996 | Carl | |
| 5,645,723 A | 7/1997 | Fujishiro | |
| 6,063,579 A | 5/2000 | Bevist et al. | |
| 6,116,099 A * | 9/2000 | Carl | 73/864.14 |
| 6,254,826 B1 * | 7/2001 | Acosta et al. | 422/65 |
| 6,358,470 B1 | 3/2002 | Higuchi | |
| 6,415,669 B1 * | 7/2002 | Carl | 73/864.14 |
| 2004/0026444 A1 * | 2/2004 | DeSilva et al. | 221/208 |

\* cited by examiner

*Primary Examiner*—Jill Warden
*Assistant Examiner*—Jyoti Nagpaul
(74) *Attorney, Agent, or Firm*—Maginot, Moore & Beck

(57) ABSTRACT

The present invention provides an improved apparatus and method for loading tips onto a pipettor. A means for applying removal force on the pipette tip box is provided so as to ensure that the box is dislodged from the pipette tips after the pipette tips have been forced onto the dispense head mandrels. In the preferred embodiment, the shuck arms are modified to incorporate springs such that when the engagement force is removed from the pipette tip box, the shuck arms are forced by the springs against the pipette tip box thereby displacing the pipette tip box from the pipette tips.

31 Claims, 6 Drawing Sheets

PIPETTE TIP BOX SHUCKING METHOD AND APPARATUS

CROSS-REFERENCE TO RELATED APPLICATIONS

This application is a continuation of U.S. patent application Ser. No. 09/324,936, filed Jun. 3, 1999 now abandoned.

FIELD OF THE INVENTION

This invention relates to pipettors generally and more particularly to an improved apparatus and method for loading pipette tips onto pipette tip mandrels.

BACKGROUND OF THE INVENTION

Biotechnology is a rapidly evolving field which is heavily dependent upon testing. Many of the procedures of interest in this field are outlined in U.S. Pat. No. 5,104,621 to Pfost et al. A common step in many of these procedures is fluid manipulation such as pipetting, diluting, dispensing and aspirating. Due to the extensive number of samples to be handled, the repetitive nature of the testing and the required precision, testing procedures are frequently automated. One device which is commonly used for the performance of fluid manipulation in an automated system is a multi-channel pipettor.

Multi-channel pipettors typically use pipette tips. In particular, disposable pipette tips provide several benefits such as minimizing the risk of cross-contamination of samples and allowing the use of tips of different sizes and shapes for different applications. However, when the multi-channel pipettor is incorporated into an automated system, problems unique to the process of fitting the multi-channel pipettor with the pipette tips arise.

Pipette tips are commonly provided in boxes for use with particular multi-channel pipettors. The boxes are normally injection molded to match the matrix pattern of the multi-channel pipettor. One of the most common multi-channel pipettors is a 96 channel pipettor having a matrix of 8 channels by 12 channels on 9 mm centers. To frictionally fit the pipette tips onto the multi-channel pipettor, the box holding the pipette tips and mandrels are moved toward each other, usually so the mandrels are inserted into the interior channel of the pipette tips. The mandrels, with the attached pipette tips, are then moved away from the pipette tip box. Ideally, the slight weight of the pipette tip box, via gravity, is sufficient to prevent the pipette tip box from binding to the pipette tips.

In order for the above process to work, the clearance between the pipette tips and the box where the tip is supported has to be made to relatively strict specifications so that each pipette tip properly aligns with a mandrel. Any variation in the alignment between the tips and the mandrels is likely to create an imprecise mating when the two are forced together. Consequently, the tip would be seated with a slight misalignment to the mandrel. While the misalignment may not affect the eventual operation to be performed by the pipettor, any time a tip is misaligned the potential exists for the box to bind on the tips rather than falling away from the tips. In addition, binding between pipette tips and a pipette tip box can also be caused by the friction between the tips and box generated by the downward pressure generated by the mandrels being forced into the pipette tips to mount the pipette tips on the mandrels.

However, as the clearances are narrowed to ensure proper alignment, the allowed misalignment before binding occurs is also narrowed. This engineering problem is further complicated by the fact that manufacturing equipment settings will drift over time. Additionally, the curing process of injection molded items, such as pipette tips and boxes, can affect the tolerances for a particular batch of tips and boxes. This problem is further exacerbated due to the number of manufacturers for boxes, each having unique system errors for their manufacturing process.

Consequently, a common malfunction of an automated system incorporating a multichannel pipettor is for the pipette tip box to bind to the tips as the tips are forced onto the mandrels. Once the box binds, a variety of consequences may be realized when the multichannel pipettor moves the mandrels with the tip box unintentionally bound to the mandrels. For example, the system may stop, requiring the operator to handle potentially dangerous materials to reset the system. Alternatively, expensive components may be damaged or dangerous substances may be spilled or splashed.

Prior systems have attempted to address this problem by providing static shucker arms on a shucker plate, and, after pipette tips have been mounted on mandrels, partially retracting the mandrels. If the pipette box is bound to the pipette tips, the box will move upward with the pipette tips as they are partially retracted. The extent to which the mandrels are retracted is enough to cause the top of the pipette tip box to touch the shucker arms, but not enough to cause the pipette tips to engage the shucker plate, which would cause the pipette tips to be de-mounted from the mandrels. Unfortunately, this mere touching of the shucker arms by the upwardly moving pipette tip box is not sufficient to consistently ensure that sufficient force is imparted to the tip box by the shucker arms to dislodge the box from the pipette tips.

What is desired, therefore, is an apparatus and method for loading pipette tips onto pipettors which ensures that the tip box does not bind on the attached tips. The apparatus and method is preferably inexpensive to realize and compatible with existing pipettors and a variety of commercially available boxes. Finally, the apparatus and method should desirably have an extremely low failure rate.

OBJECTS OF THE INVENTION

It is an object of the present invention to provide an apparatus and method which is a reliable means of controlling the tip box position during pipette tip loading and unloading.

Another object of the invention is to provide a system and method that is usable with a variety of tips and tip boxes from different manufacturers.

Another object of the invention is to reduce susceptibility to binding in the loading process due to manufacturing tolerance buildup in molded tip boxes and pipette tips.

Another object of the invention is to provide a solution to tip box binding which can be easily incorporated into existing pipettors.

Further, it is an object to realize the above advantages in an uncomplicated and inexpensive fashion.

SUMMARY OF THE INVENTION

The present invention is an improved apparatus and method for the placing of tips onto the mandrels of a pipettor. In one embodiment, extendable shucking arms are provided which force the box holding the pipette tips off of the tips after the tips are frictionally attached to the mandrels of the pipettor. In operation, the pipette tips are initially seated within a pipette tip box. The pipette tips are seated onto the pipettor mandrels by moving the pipette tips and the mandrels toward each other. Once the pipette tips are seated on the mandrels, a removal force is applied to the box to aid in overcoming any binding between the pipette box and the pipette tips, and to thereby ensure separation of the pipette tips from the pipette box.

DETAILED DESCRIPTION

Figure 1:
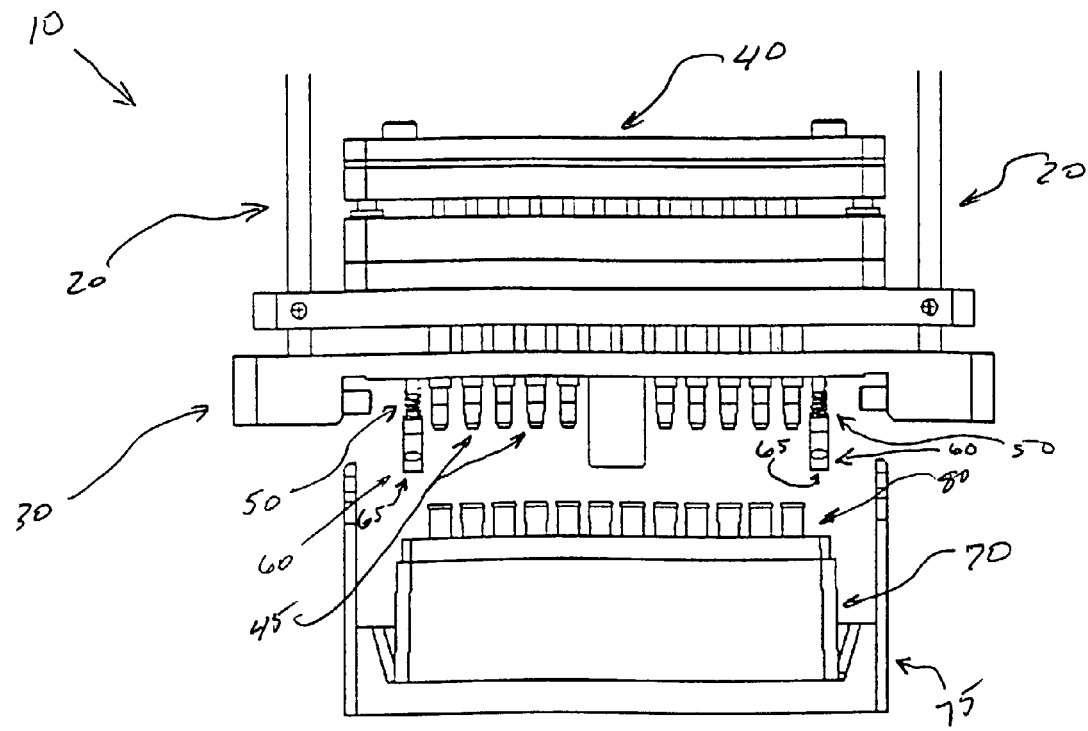
FIG. 1 shows a dispense head assembly in a retracted position over a pipette tip box.

Referring now to FIG. 1, one embodiment of a pipettor according to the present invention is described. The dispense head assembly in this embodiment is a commercially available dispense head found on a MultiMek 96 Channel Pipettor available from Carl Creative Systems of Harbor City, Calif. The Dispense head assembly is initially held in place above pipette tip box 70 by control arms 20. Plurality of mandrels 45 of mandrel holder 40 extend through shuck plate 30 and are aligned with pipette tips 80. Pipette tips 80 are held in place by pipette tip box 70. The combination of pipette tips 80 and pipette tip box 70 is in turn held in position by tip box holder 75.

Figure 2:
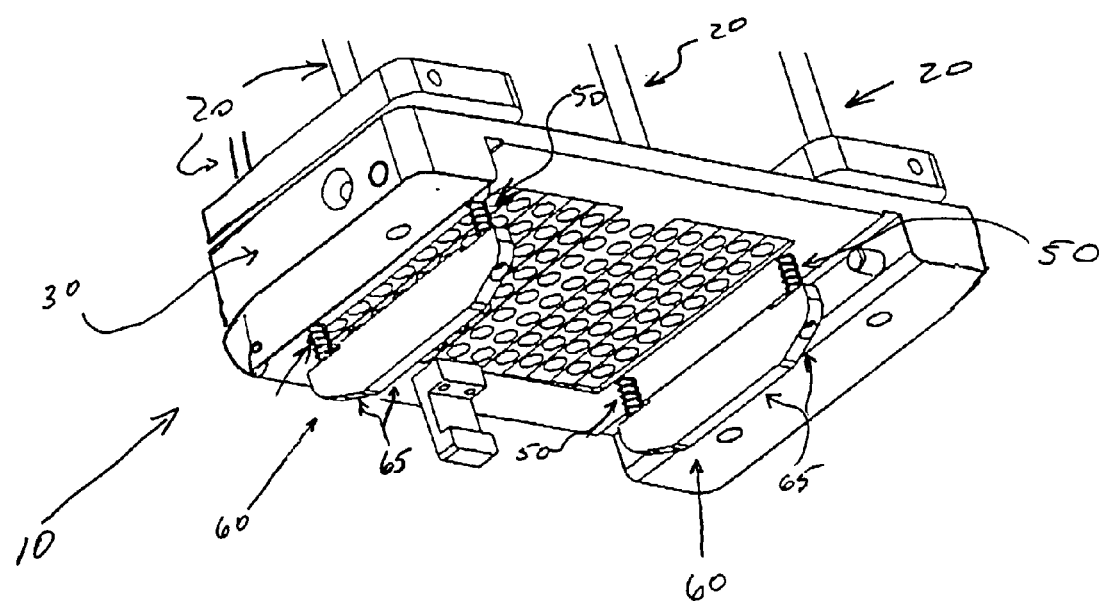
FIG. 2 shows a dispense head assembly.
Figure 3:
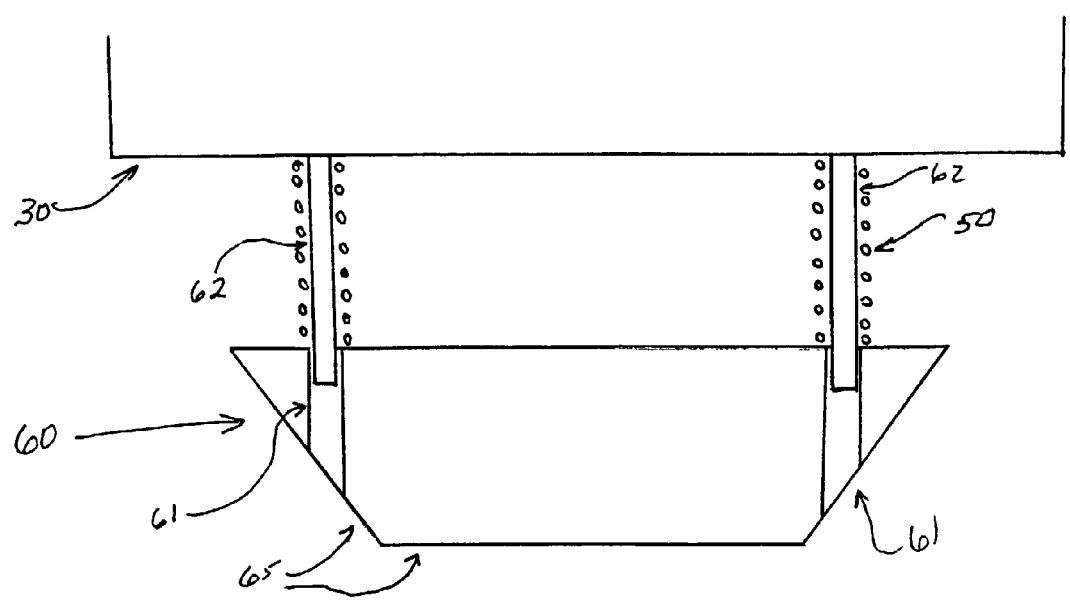
FIG. 3 shows a cutaway view of a shucking arm.

In this embodiment, when loading is not in progress, shucking arms 60 are forced downward to an extended position by forcing means. Forcing means is provided by springs 50, positioned intermediate to shuck plate 30 and to shucking arms 60 as shown in FIG. 2. Referring now to FIG. 3, shucking arms 60 have channels 61. Guides 62 of shuck plate 30 are slidably located within springs 50 and channels 61. Contact edges 65 are provided on shucking arms 60.

Figure 4:
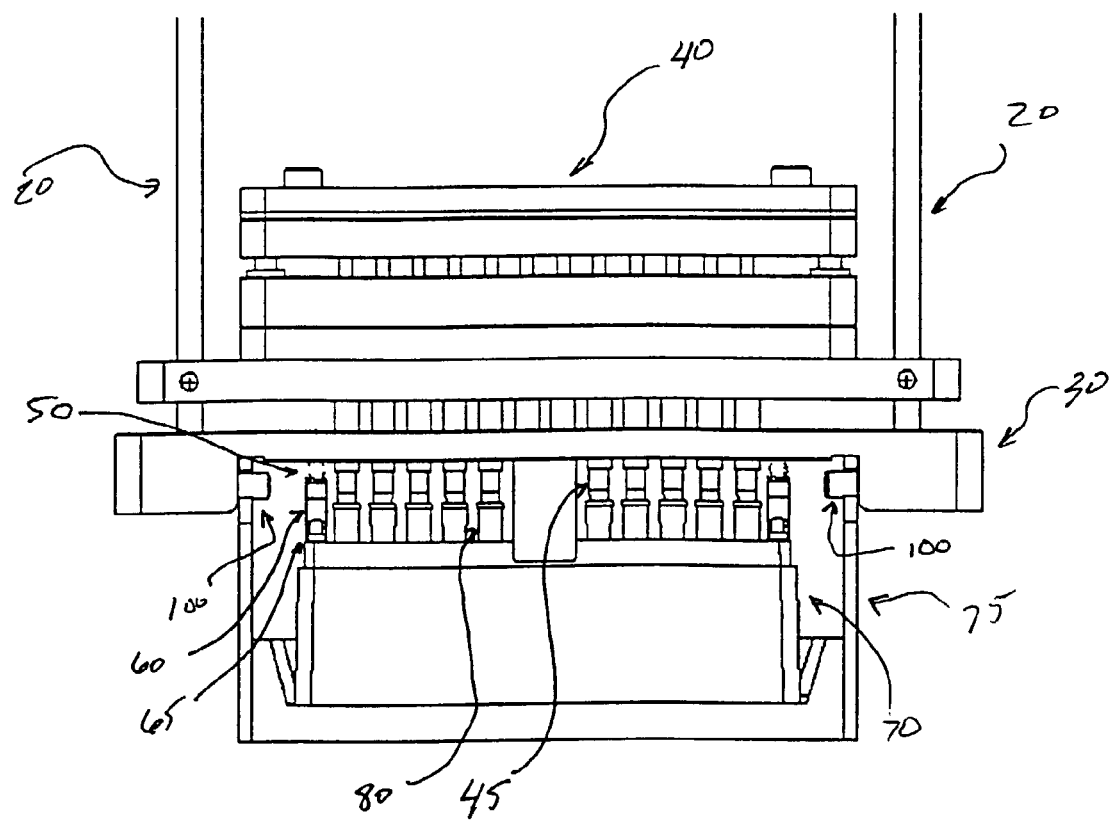
FIG. 4 shows a dispense head assembly in an extended position engaging a pipette tip box.

Referring again to FIG. 1, the loading operation is described. Control arms 20 are moved downward such that contact edges 65 approach pipette tip box 70 which contains pipette tips 80. Referring now to FIG. 4, pipette tip box 70 engages shucking arms 60 at contact edges 65, thereby forcing springs 50 into compression. Shucking arms 60 are maintained in alignment with shuck plate 30 as springs 50 are compressed by guides 62 which are slidably positioned within channels 61 of shuck arms 60. Once springs 50 are compressed, pins 100 of shuck plate 30 are moved horizontally to engage slots 74 in tip box holder 75.

It will be appreciated that in accordance with the present invention, the system may be configured for use with pippette tip boxes of different shapes. One variable among pipette tip boxes is the height of the boxes in the area contacted by shucking arms 60. Those of skill in the art will therefore appreciate the desirability of ensuring that the travel distance between shucking arms 60 and shuck plate 30, should be sufficient to accommodate the height of the shortest pipette tip box with which the invention may be used.

Pipette tips 80 may be mounted, for example by being frictionally seated, onto mandrels 45 by means for moving a plurality of pipette tips and the plurality of mandrels toward each other to thereby cause the pipette tips to become mounted on the mandrels; for example, by shuck plate 30 applying upward engaging pressure on tip box holder 75 through pins 100 while pipette tip box 70 provides support for pipette tips 80 as well as aligning pipette tips 80 with mandrels 45. It is important that the forcing means, springs 50 in this embodiment, have sufficient travel to allow pipette tips 80 to be mounted onto mandrels 45.

Figure 5:
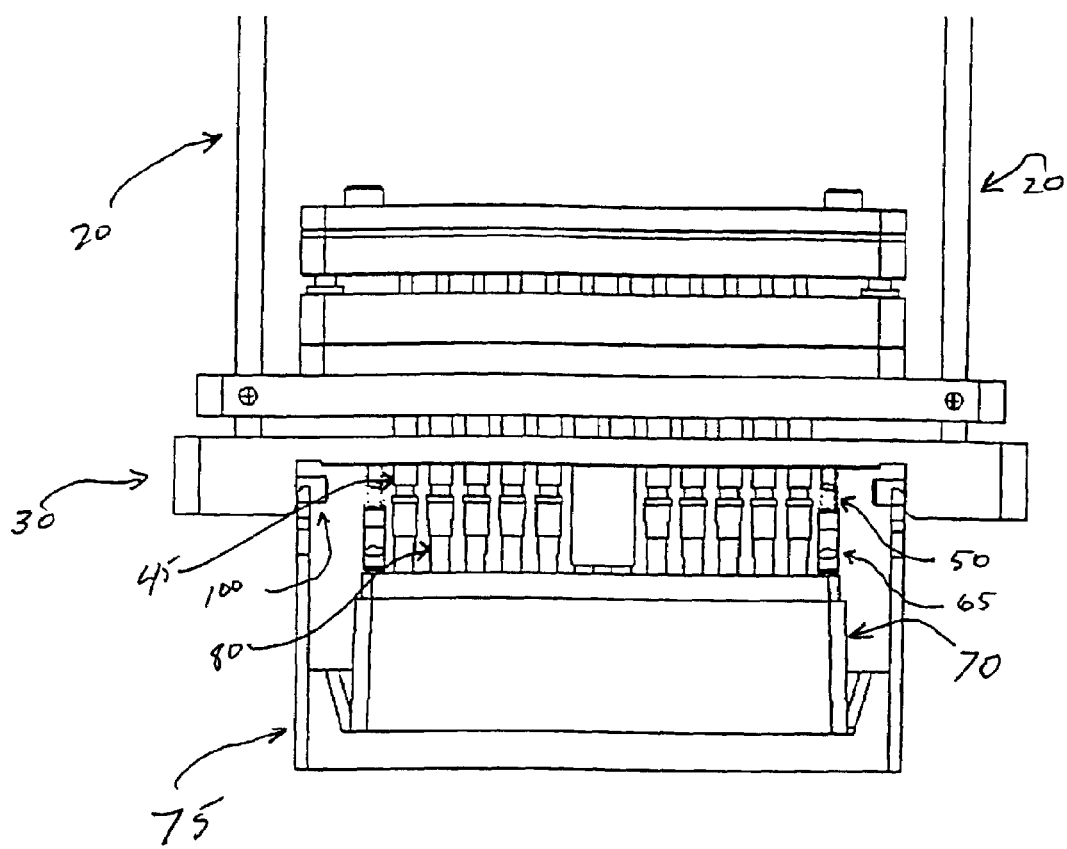
FIG. 5 shows a pipette tip box being removed from a dispense head assembly with pipette tips mounted on the mandrels.
Figure 6:
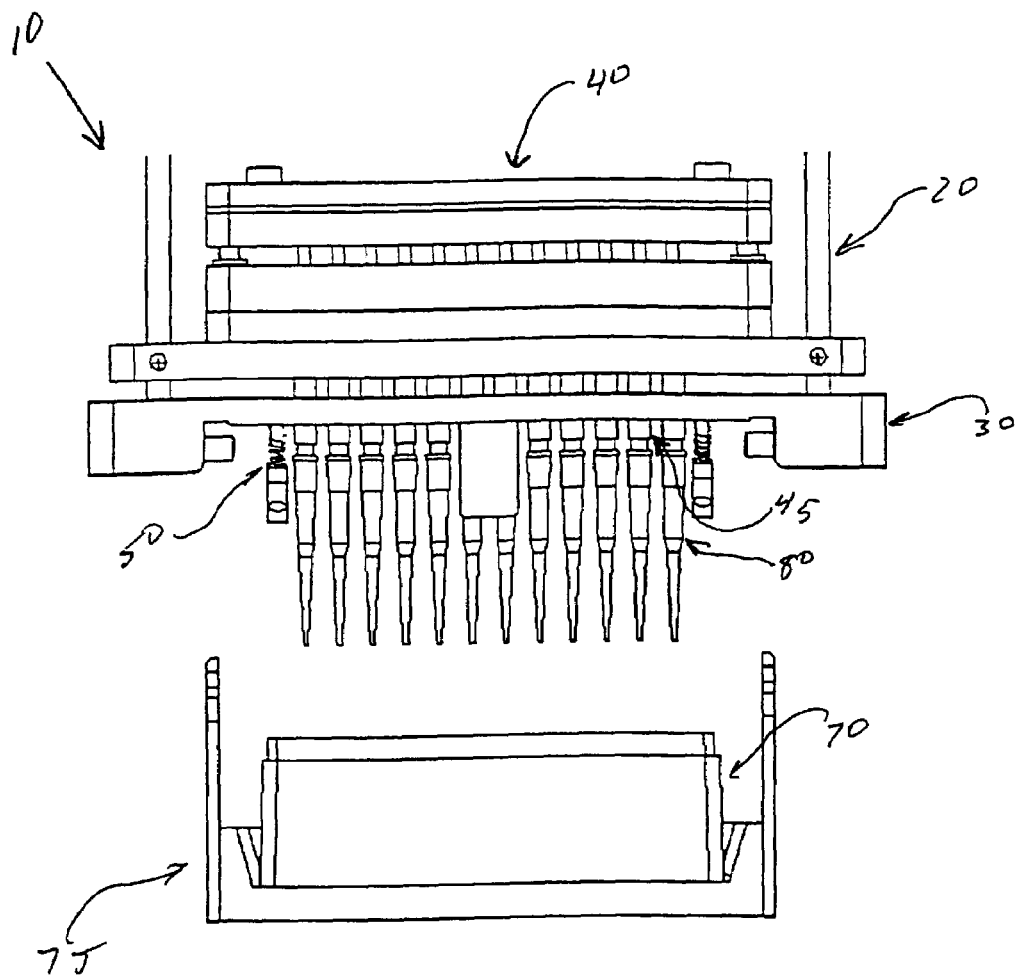
FIG. 6 shows pipette tips attached to mandrels with the pipette tip box removed.

Referring now to FIG. 5, after pipette tips 80 are seated onto mandrels 45, the engaging pressure is relieved by partially extending control arms 20, and moving the control arms 20 horizontally, moving pins 100 of shuck plate 30 out of slots 74 of tip box holder 75 to disengage therefrom. Control arms 20 then partially retract thereby partially retracting dispense head assembly 10, thus moving mandrels 45 with pipette tips 80 mounted thereon in a direction opposite the direction of movement used to cause pipette tips 80 to engage mandrels 45. This movement should be of a distance sufficient to allow the plurality of mandrels 45 with the plurality of pipette tips 80 mounted thereon to permit the pipette tip box to become dislodged from the pipette tips. However, it is possible that, but for the shucking arms 65 described below, pipette tip 70 box could bind to pipette tips 80. Accordingly, as dispense head assembly 10 and shuck plate 30 move away from tip box holder 75, springs 50 and shucking arms 65 apply a mechanical force against tip box 70 to thereby move pipette tip box 70 away from pipette tips 80 mounted on mandrels 45. The removal force supplied by spring 50 is sufficient to overcome any frictional binding between tip box 70 and pipette tips 80. Accordingly, in the disclosed representative embodiment, shucking arms 65 comprise means for applying a mechanical force to pipette tip box 70 to thereby move pipette tip box 70 away from pipette tips 80 mounted on mandrels 45. In this embodiment, It is desirable that sufficient momentum be imparted to pipette tip box 70 so that pipette tip box 70 clears any binding caused by misalignment of pipette tips 80. Consequently, as shown in FIG. 6, tip box 70 stays positioned within tip box carrier 75 as dispense head assembly 10 is retracted.

In this embodiment, removal force was provided by springs 50 acting against shucking arms 60. However, other embodiments and configurations can be used. Examples of alternative embodiments include mechanisms to apply a mechanical force to the pipette tip box to thereby move the pipette tip box 70 away from pipette tips 80 mounted on mandrels 45, such as a clamp, latching mechanism or a vacuum source which provides a suction on the bottom of pipette tip box 70, diagrammatically shown as 101 of FIG. 5, or the use of shucking arms formed of resiliently compressible material in lieu of springs or some other bias inducing mechanism. It is also within the scope of the invention to use some other device, such as a solenoid or compressed air source, to contact the pipette tip box 70, either downwardly or laterally, to provide sufficient movement of the pipette tip box 70 to dislodge it from the pipette tips if it is bound thereto. Alternatively, instead of two shucking arms, a single arm that matches the contour of the upper periphery of the pipette tip box, or even a narrow centrally disposed arm that contacts the pipette tip box between several of the pipette tips, could be employed.

Moreover, different mechanism for moving the pipette tips toward the mandrels are possible. For example, tip box holder 75 is unnecessary, as the mandrels could be forced downward toward the pipette tips instead of forcing the tip box upward toward the mandrels. Moreover, the system could also be configured with mandrels that engage the exterior of the pipette tips instead of being forced into the interior channels of the pipette tips. These alternative embodiments are within the scope of the present invention.

In accordance with the present invention, an apparatus and method of use is provided which is useful in a wide variety of applications for a variety of machines and with pipette tip boxes from many different manufacturers. The invention is extremely reliable, and easily practiced on pre-existing pipettors. The invention can be uncomplicated to practice and very economical to incorporate into an automated system.

What is claimed is:

1. A method for mounting a plurality of pipette tips positioned in a pipette tip box onto a plurality of mandrels of a multi-channel pipettor, the multi-channel pipettor having a shuck plate for contacting the plurality of pipette tips and removing the plurality of pipette tips from the plurality of mandrels, the method comprising the steps of:
   (A) moving the plurality of pipette tips and the plurality of mandrels relative to each other such that the pipette tips to become mounted on the mandrels;
   (B) moving the plurality of mandrels with the plurality of pipette tips mounted thereon in a direction away from the pipette tip box to attempt removal of the pipette tips from the pipette tip box;
   (C) applying a downward mechanical force to the pipette tip box using a means for applying a mechanical force, the means for applying a mechanical force including a surface of the multi-channel pipettor configured to contact the pipette tip box and move independent of the shuck plate, the downward mechanical force separating the pipette tip box from the pipette tips mounted on the mandrels.

2. The method of claim 1, wherein the means for applying a mechanical force comprises at least one spring.

3. The method of claim 2 wherein the means for applying a mechanical force further comprises at least one shucking arm and the at least one spring operates against at least one shucking arm.

4. The method of claim 3 wherein at least one guide extends from the shuck plate and the at least one shucking arm is slideably positioned upon the at least one guide.

5. The method of claim 1, wherein the means for applying a mechanical force comprises a resiliently compressible member.

6. The method of claim 1 wherein at least one guide extends from the shuck plate and the means for applying a mechanical force comprises at least one shucking arm that is slideably positioned upon the at least one guide.

7. The method of claim 6 wherein the at least one guide is static with respect to the shuck plate.

8. The method of claim 1 wherein the means for applying a mechanical force comprises at least one shucking arm having an elongated contact edge, and the elongated contact edge contacts the pipette tip box when the downward mechanical force is applied to the pipette tip box.

9. The method of claim 8 wherein the at least one shucking arm comprises two shucking arms having elongated contact edges applied to opposite sides of the pipette tip box when the downward mechanical force is applied to the pipette tip box.

10. A multi-channel pipettor comprising:
    a plurality of mandrels for mounting a plurality of pipette tips positioned in a pipette tip box;
    means for moving the plurality of pipette tips and the plurality of mandrels relative to each other such that the pipette tips become mounted on the mandrels;
    a shuck plate for contacting the pipette tips and removing the pipette tips mounted on the mandrels;
    a means for applying a mechanical force including a surface configured to contact the pipette tip box and move independent of the shuck plate, the means for applying a mechanical force applying a downward mechanical force to the pipette tip box to force the pipette tip box away from the pipette tips mounted on the mandrels.

11. The multi-channel pipettor of claim 10, wherein the means for applying a mechanical force comprises at least one spring.

12. The multi-channel pipettor of claim 11 wherein the means for applying a mechanical force further comprises a shucking arm biased by the at least one spring.

13. The multi-channel pipettor of claim 11 wherein the means for applying a mechanical force further comprises at least one guide extending from the shuck plate, the least one shucking arm slideably positioned upon the at least one guide.

14. The multi-channel pipettor of claim 10 wherein the means for applying a mechanical force comprises a resiliently compressible member.

15. The multi-channel pipettor of claim 10 further comprising at least one guide extending from the shuck plate.

16. The multi-channel pipettor of claim 15 wherein the means for applying a mechanical force comprises at least one shucking arm that is slideably positioned upon the at least one guide.

17. The multi-channel pipettor of claim 15 wherein the at least one guide is static with respect to the shuck plate.

18. The multi-channel pipettor of claim 10 wherein the means for applying a mechanical force comprises at least one shucking arm having an elongated contact edge.

19. A multi-channel pipettor comprising:
    a matrix of mandrels, each mandrel capable of receiving a pipette tip positioned in a pipette tip box;
    means for moving the matrix of mandrels, the means for moving the matrix of mandrels operable to move the matrix of mandrels in a first direction toward a matrix of pipette tips positioned in a pipette tip box to thereby cause the pipette tips to engage the mandrels, the means for moving the matrix of mandrels also operable to move the matrix of mandrels with the pipette tips thereon in a second direction opposite the first direction;
    means for removing the pipette tips from the mandrels; and
    forcing means for contacting the pipette tip box and moving the pipette tip box in the first direction during movement of the matrix of mandrels in the second direction to thereby separate the pipette tip box from the pipette tips mounted on the mandrels, the forcing means for contacting the pipette tip box and moving the pipette tip box in the first direction moving independent of the means for removing the pipette tips from the mandrels.

20. A pipettor comprising:
    (a) a plurality of mandrels for mounting a plurality of pipette tips positioned in a pipette tip box;

(b) a shuck plate for removing the plurality of pipette tips mounted on the plurality of mandrels from the plurality of mandrels, retraction of the plurality of mandrels into the shuck plate causing the plurality of tips to be removed from the plurality of mandrels; and (c) at least one shucking arm, the at least one shucking arm operable to apply a downward mechanical force to the pipette tip box to thereby move the pipette tip box away from the plurality of pipette tips upon mounting of the plurality of pipette tips on the plurality of mandrels without retraction of the plurality of mandrels into the shuck plate.

21. The pipettor or claim 20 wherein the at least one shucking arm is moveable relative to the shuck plate.

22. The pipettor of claim 21 further comprising a spring positioned between the shuck plate and the at least one shucking arm.

23. The pipettor of claim 22 further comprising a guide extending from the shuck plate and a channel formed in the at least one shucking arm, wherein the guide extends into the channel and the spring is retained upon the guide.

24. A method of mounting a plurality of pipette tips positioned in a pipette tip box to a plurality of mandrels of a pipettor, the pipettor including a shuck plate such that the plurality of mandrels are disposed to extend through the shuck plate and are also operable to be at least partially retracted into the shuck plate, the method comprising the steps of:

a. extending the plurality of mandrels through the shuck plate and moving the plurality of pipette tips and the plurality of mandrels toward each other to thereby cause the pipette tips to become mounted on the portion of the mandrels extending through the shuck plate;

b. moving the plurality of mandrels with the plurality of pipette tips mounted thereon in a direction away from the pipette tip box to attempt removal of the plurality of pipette tips from the pipette tip box;

c. applying a downward mechanical force to the pipette tip box using a shucking arm, the downward force applied without retraction of the plurality of mandrels into the shuck plate, the downward mechanical force thereby separating the pipette tip box from the plurality of pipette tips mounted on the plurality of mandrels.

25. The method of claim 24 wherein the shucking arm is capable of independent movement with respect to the shuck plate.

26. The method of claim 25 wherein a guide extends from the shuck plate and the shucking arm is slideably positioned upon the guide.

27. The method of claim 26 wherein a spring is positioned between the shuck plate and the shucking arm to bias the shucking arm away from the shuck plate.

28. The method of claim 27 wherein a channel is formed in the shucking arm such that the guide extends into the channel and the spring is retained upon the guide.

29. A multi-channel pipettor comprising:

a shuck plate comprising a plurality of holes;

a plurality of mandrels extending through the holes in the shuck plate, the plurality of mandrels configured to receive a plurality of pipette tips positioned in a pipette tip box; and a contact surface configured to move independent of the shuck plate and engage the pipette tip box, wherein the contact surface is adapted apply a force to the pipette tip box in a direction that encourages the pipette tip box away from the plurality of mandrels.

30. The multi-channel pipettor of claim 29 wherein the contact surface is provided on a shucking arm operable to move independent of the shuck plate.

31. The multi-channel pipettor of claim 29 wherein the contact surface is moveably connected to the shuck plate.

* * * * *